(12) United States Patent
Kask

(10) Patent No.: US 7,019,310 B2
(45) Date of Patent: Mar. 28, 2006

(54) METHOD OF ANALYSIS OF SAMPLES BY DETERMINATION OF A FUNCTION OF SPECIFIC BRIGHTNESS

(75) Inventor: Peet Kask, Harku (EE)

(73) Assignee: Evotec AG, Hamburg (DE)

( * ) Notice: Subject to any disclaimer, the term of this patent is extended or adjusted under 35 U.S.C. 154(b) by 0 days.

(21) Appl. No.: 09/029,830

(22) PCT Filed: Nov. 10, 1997

(86) PCT No.: PCT/EP97/05619

§ 371 (c)(1),
(2), (4) Date: Mar. 10, 1998

(87) PCT Pub. No.: WO98/16814

PCT Pub. Date: Apr. 23, 1998

(65) Prior Publication Data

US 2003/0013086 A1    Jan. 16, 2003

(30) Foreign Application Priority Data

Oct. 12, 1996  (EP) ................................. 96116373

(51) Int. Cl.
*G01N 21/64* (2006.01)
(52) U.S. Cl. ................................. 250/459.1
(58) Field of Classification Search ........ 356/301–307, 356/318, 335–337; 250/459.1; 436/514, 436/518; 530/414, 415
See application file for complete search history.

(56) References Cited

U.S. PATENT DOCUMENTS

| 4,768,879 A | | 9/1988 | McLachlan et al. ........ 356/301 |
| 4,788,443 A | | 11/1988 | Furuya ....................... 250/574 |
| 5,763,585 A | * | 6/1998 | Nag ........................... 530/413 |

FOREIGN PATENT DOCUMENTS

EP    0601714    6/1994

OTHER PUBLICATIONS

H. Quian, et al., *Proc. Natl. Acad. Sci.*, vol. 87, Jul. 1990, pp. 5479-5483.
SM. NIE, et al., *Analytical Chemistry*, vol. 67, No. 17, Sep. 1, 1995, pp. 2849-2857.
Rigler et al. "Fluorescence correlation spectroscopy with high count and low background: analysis of translational diffusion." Eur. Biophys. J. (1993) 22: 169-175.

* cited by examiner

*Primary Examiner*—Padmashri Ponnaluri
*Assistant Examiner*—Jon D. Epperson
(74) *Attorney, Agent, or Firm*—Jacobson Holman PLLC

(57) ABSTRACT

A method for characterizing samples having units, by monitoring fluctuating intensities of radiation emitted, scattered and/or reflected by said units in at least one measurement volume, the monitoring being performed by at least one detection means, said method comprising the steps of:
a) measuring in a repetitive mode a number of photon counts per time interval of defined length,
b) determining a function of the number of photon counts per said time interval,
c) determining a function of specific brightness of said units on basis of said function of the number of photon counts.

20 Claims, 12 Drawing Sheets oligo A oligo B

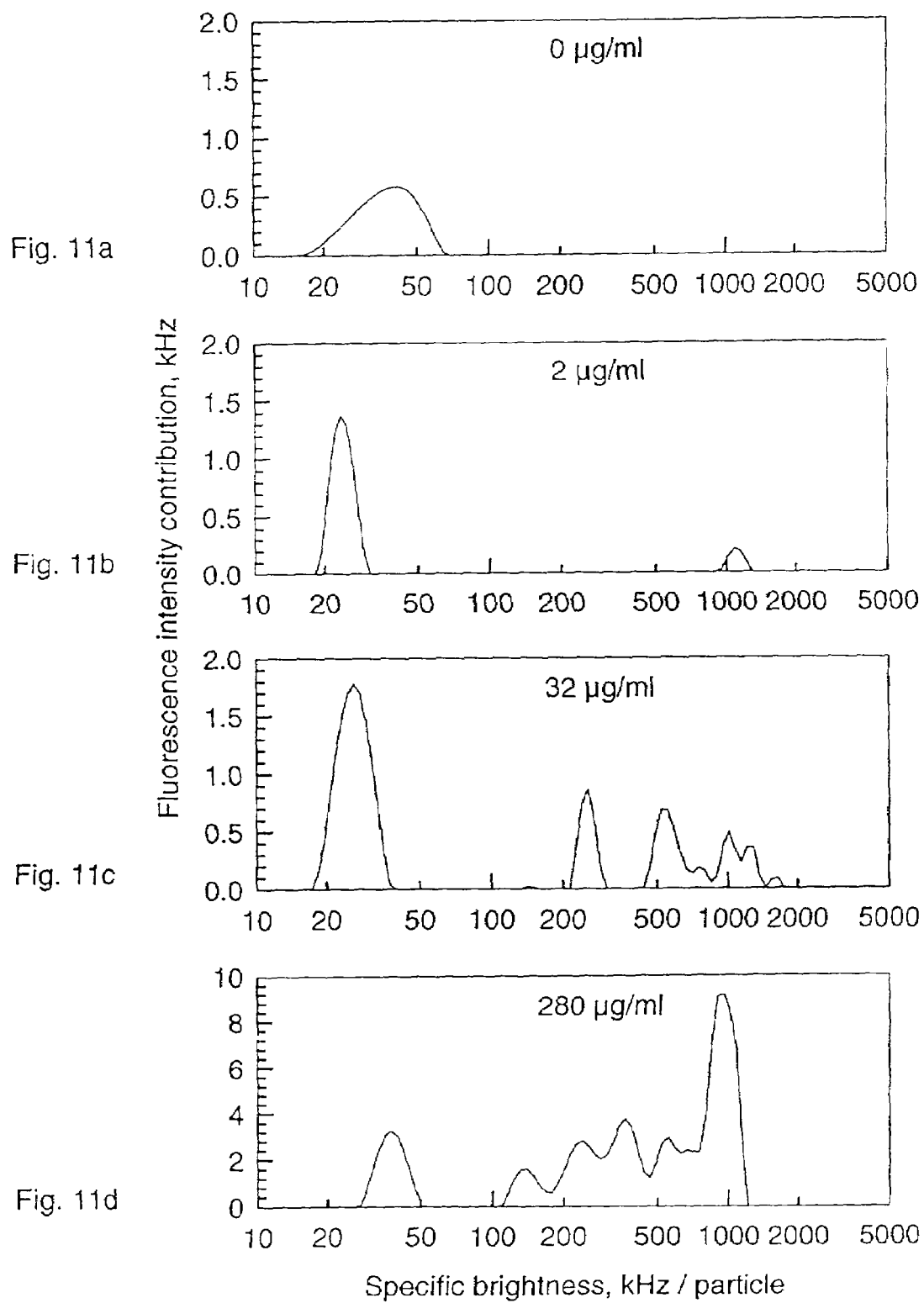

METHOD OF ANALYSIS OF SAMPLES BY DETERMINATION OF A FUNCTION OF SPECIFIC BRIGHTNESS

The present invention relates to a method for characterizing samples having units which emit, scatter and/or reflect radiation by measuring in a repetitive mode a number of photon counts per time interval of defined length and determining a function of the number of photon counts.

The first successful studies on fluorescence intensity fluctuations were performed by Magde, Elson and Webb (Biopolymers, Vol. 13, 29–61, 1974) who demonstrated the possibility to detect number fluctuations of fluorescent molecules and established a research field called fluorescence correlation spectroscopy (FCS). FCS was primarily developed as a method for determining chemical kinetic constants and diffusion coefficients. The experiment consists essentially in measuring the variation with time of the number of molecules of specific reactants in a defined open volume of solution. The concentration of a reactant is measured by its fluorescence from a small measurement volume. The measurement volume is defined by a focused laser beam, which excites the fluorescence, and a pinhole in the image plane of the microscope collecting fluorescence. Intensity of fluorescence emission fluctuates in proportion with the changes in the number of fluorescent molecules as they diffuse into and out of the measurement volume and as they are created or eliminated by the chemical reactions. Technically, the direct outcome of an FCS experiment is the calculated autocorrelation function of the measured fluorescence intensity.

An important application of FCS is determination of concentrations of fluorescent species having different diffusion rates, in their mixture. In order to separate the two terms in the autocorrelation function of fluorescence intensity corresponding to translation diffusion of two kinds of particles, at least about a two-fold difference in diffusion time is needed, which corresponds to an eight-fold mass difference of particles. Furthermore, even if one succeeds in separating the two terms in the autocorrelation function of fluorescence intensity, it is yet not sufficient for determining the corresponding concentrations except if one knows the relative brightness of the two different types of particles.

Whereas conventional FCS yields rather limited information about aggregate sizes from a simple autocorrelation function of fluorescence intensity fluctuations, possible biophysical applications demand the ability to analyse complex mixtures of different species. For that purpose, Palmer and Thompson studied higher order correlation functions of fluorescence intensity fluctuations and have outlined methods for determining the number densities and relative molecular brightness of fluorescence of different fluorescent species (Biophys. J., Vol. 52, 257–270, August 1987). Their technique may in principle proof useful in detecting and characterizing aggregates of fluorescent-labeled biological molecules such as cell surface receptors, but has a major disadvantage of being rather complex, so that data processing of an experiment including the calculation of high-order correlation functions lasts hours.

A considerably less complicated method than calculation of high order auto-correlation functions for characterizing mixtures of fluorescent species of different specific brightness is calculation of higher order moments of fluorescence intensity out of the experimentally determined distribution of the number of photon counts. This method was presented by Qian and Elson (Biophys. J., Vol. 57, 375–380, February 1990; Proc. Natl. Acad. Sci. USA, Vol. 87, 5479–5483, July 1990). In their demonstration experiments signal acquisition times of about 7 minutes were used for a relatively favourable experimental system of two kinds of fluorescent particles which differed by 30-fold in their specific brightness, the mixture of monomers and 30-mers. The method of moments is relatively simple and fast in calculations, but it allows to determine only a limited number of unknown parameters characterizing the sample because usually only about three or four first moments of fluorescence intensity can be calculated from the experiment with precision sufficient for further analysis.

Because of this reason, the method of moments is hardly suitable for characterizing complex samples or selecting between competing models of the sample or checking whether the given model is appropriate.

One object of the invention is to obtain reliable information about a sample having units emitting, scattering and/or reflecting photons, which renders possible an analysis of the sample wish respect to certain ingredients or with respect to certain states of the sample.

Another object of the present invention is to substantially extend the useful information obtainable from the experimentally determined function, preferably distribution of the number of photon counts.

The objects of the present invention are solved with the method having the features of claim 1.

The term "unit of a sample" refers, in general, to subparts of the sample which are capable of emitting, scattering and/or reflecting radiation. A sample might contain a number of identical units or different units which preferably can be grouped into species. The term "different species" refers also to different states, in particular different conformational states, of a unit such as a molecule. Fluorescently labelled or naturally fluorescent molecules, molecular complexes, vesicles, cells, beads and other particles in water or other liquids are examples of fluorescent units in liquid samples, while examples of fluorescent units of a solid sample are impurity molecules, atoms or ions, or other fluorescence centers.

What is meant by the term "specific brightness" of units in the sense of the present invention is a physical characteristic expressing in what extent a unit of given species is able to emit, scatter and/or reflect radiation, preferably light. It is thought to characterize single units, preferably particles, and therefore the value of specific brightness is not depending on concentration of the units, neither on the presence of other units. Thus, a change of the total count rate of photons emitted, scattered and/or reflected from the measurement volume, if only due to a change in concentration of the total number of units, does not influence the measured value of specific brightness and the value of the ratio of numbers of units of different species determined by the present invention. Specific brightness is usually expressed in terms of the mean count rate per unit which is a weighted average of the count rate over coordinates of the unit in the measurement volume. In some cases, one might prefer to express specific brightness in count rates corresponding to a unit positioned in a place where the count rate has its top values. This could e.g. be the center of the focus of an incident beam.

The importance of the present invention for the analysis of samples may be illustrated by the following, non-limiting example: Assuming that a solution contains a quantity (a) of one type of particles (A) with a respective specific brightness (Ia) and a quantity (b) of another type of particles (B) with a respective specific brightness (Ib), the overall count rate of photons emitted by the solution depends on the expression Ia*a+Ib*b. Thus, by mere determination of the overall count rate, it is not possible to dissolve the value of a and/or b. Generally, in fluorimetric measurements, the overall count rate of at least one type of particles is determined in an independent experiment. If the total number a+b of particles does not change with respect to this measurement, the ratio a/b or its inverse can be determined by mere determination of the overall count rate of the mixture in a second measurement. However, the assumption, that the total number a+b does not change between the two measurements, is often wrong. For example, adsorption effects of particles to surfaces may occur. Fluorimetric measurements cannot verify the total number of particles a+b independently. The present invention overcomes these restrictions. From one measurement, the numbers of particles a and b can be determined without any prior information of their respective specific brightnesses.

It is to be understood that the following description is intended to be illustrative and not restrictive. Many embodiments will be apparent to those of skill in the art upon reviewing the following description. By way of example, the invention will be described primarily with reference to measuring numbers of photon counts from light emitted by fluorescently labelled particles in a sample. For example, in some embodiments it may be desirable to measure numbers of photon counts of other origin than fluorescence.

The present invention provides a method for calculating the expected function, preferably the distribution of the number of photon counts corresponding to given real equipment and samples of given composition. The ability to predict the distribution of the number of counts corresponding to samples to given composition allows, when studying samples of unknown composition, to find out the model of the sample yielding the closest fit between the calculated and the experimentally determined distribution of the number of photon counts. What is meant by the composition of the sample here is the specific brightness and concentration of units present in the sample. For example, a solution of a single fluorescent dye is characterized by two parameters: the concentration and specific brightness of the dye molecules. A mixture of two fluorescent dyes is characterized by four parameters: the concentrations and specific brightnesses of the two kind of molecules. A complex mixture can be characterized by the distribution function of concentration versus specific brightness of molecules. Conveniently, concentration is expressed as the mean number of units per measurement volume, and specific brightness is expressed as the mean count rate per unit. Preferably said units are particles.

From the other side, the function, e.g. the distribution of the number of photon counts depends not only on composition of the sample, but also on equipment: first of all, on the spatial brightness function characteristic to the optical set-up, and on some characteristics of the detector like its dark count rate, its dead time and probability of afterpulsing. In the interest of a high quality of analysis, which is indicated by achieving a close fit between the experimentally determined and the calculated curves, it is preferred to characterize the equipment adequately.

Claim 1 does not cover the method described by Qian and Elson, as their method compares estimated and calculated moments of the distribution of light intensity, but not directly the distribution of the number of photon counts. Qian and Elson's teaching misses the teaching of the present invention.

According to the invention, a new quality of analysis of samples containing units, preferably particles, which emit, scatter and/or reflect radiation, preferably light, becomes possible. In a first step, a number of photon counts from radiation emitted, scattered and/or reflected by the units in the sample is measured per time interval of defined length in a repetitive mode. A series of different time intervals can also be used for a more complex analysis. In step 1, the number of photon counts is measured in a repetitive mode, i.e. the number of detected photons is counted preferably many times, repeating the procedure in a series of preferably consecutive time intervals, in order to obtain statistically meaningful data. The length of the time interval is the duration of the time interval during which the number of photon counts is determined. The length of the time interval is usually expressed in microseconds or milliseconds or other units of time.

In a second step of the method according to the invention, a function, preferably a distribution of the number of photon counts per said time interval is determined, which means that it is determined how many times one has obtained a certain number of photon counts. The distribution is a function of the number of photon counts, expressing either the relative or absolute number of observed (or expected) events when a particular number of photon counts was (or is) obtained.

In a third step, the experimentally determined distribution of photon counts is analyzed directly without intermediate steps to obtain a function, preferably a distribution of specific brightnesses of the units in the sample.

It is preferred that at least one detection means monitors said number of photon counts. Any detector which is capable to detect radiation emitted, scattered and/or reflected by units of the sample may be used, said radiation arising preferably out of at least one measurement volume. Appropriate detection means such as an avalanche photo-diode, a photomultiplier or conventional photo-diodes are well known to those of skill in the art. It might also be preferred to use a multidetector consisting of a monolithic configuration of a plurality to detectors, especially if one wants to measure a set of samples in parallel as it is the case in miniaturized high throughput screening. It might further be preferred to use a two-dimensional multi-array detector.

In the sense of the present invention, particles are preferably luminescently labelled or unlabelled, preferably naturally luminescent, molecules or macromolecules, or dye molecules, molecular aggregates, complexes, vesicles, cells, viruses, bacteria, beads, or mixtures thereof.

The luminescence properties of the units can be varied by conjugating them with a specific luminophore via different linker molecules. It might be preferred to use polymeric linker molecules consisting of a varying number of equal or different monomers.

It may be advantageous to provide at least one of the units with a specific site to which an affinity substance having detectable properties will bind.

In a preferred embodiment, at least one of the units has a tag of histidine residues to which an affinity substance such as a chelate complex can bind. It might be preferred to use complexes of nickel-nitrilotriacetic acid (Ni-NTA) and a luminescence label as said affinity substance. In a further preferred embodiment, said complex contains two or more chelating groups and at least one luminescence label.

The luminescence properties of the units may also be varied by conjugating them with a first molecule, as e.g. biotin, which binds a luminescently labelled second molecule, as e.g. luminescently labelled avidin or streptavidin, or vice versa as it is described in detail in example 3.

Luminescence properties of a unit can also be changed by energy transfer. Energy absorbed by a donor is transferred upon close contact to a luminophore of an acceptor and subsequently emitted.

In a further preferred embodiment, the units, preferably particles, each carry a number of binding sites for luminescent particles. Luminescent particles can directly or via secondary molecules bind to these binding sites. Since highly luminescent particles are generated when many luminescent particles bind to the binding sites of the first particles, the method according to the invention is able to distinguish easily between particles with a large difference in luminescence intensity, so that even a small amount of bound luminescent particles can be measured in presence of an excess concentration of free luminescent particles. This embodiment provides a new analysis of particles which do not carry a luminescent label by binding to a second particle which is luminescently labelled, but whose brightness does not change upon binding. A commercially very important application of this method is the measurement of fluorescently labelled antibodies binding to an antigen, while the antigen is binding to at least one of the multiple binding sites of the particle which is preferably a bead, or vice versa. The method can also be applied to other types of interactions such as nucleic acid hybridization or protein/nucleic acid interaction. The invention can also be applied for the analysis of distribution characteristics of said particles, such as for quality control and process control of polymers or oligomeric suspensions of particles. In addition, surface areas of particles can be analyzed as well as distributions of surface areas of particles.

In a preferred embodiment, one type of particle, subsequently denoted A, carries more than one binding site. Another, luminescent type of particles, subsequently denoted C, can bind (i) either directly to at least one of the binding sites of particle A, or (ii) binds to at least one binding site of a molecule B, which in turn binds to at least one of the binding sites of particle A. These bindings may be mediated either by naturally occurring binding sites on the particles, or mediated by introduction of specific binding sites to the particles A, B and/or C. Since in both cases more than one of the particles of type C may band to particle A, the complex will emit more photons than free particles of type C. This embodiment provides a convenient way to measure binding of particles of type B to a particle of type C or A, although the particle of type B is not luminescently labelled.

In a further preferred embodiment, the measurement volume is only a part of the total volume of the sample and said units, preferably particles, are diffusing and/or being actively transported into and out of said measurement volume and/or the sample is actively transported and/or optically scanned. If said units, e.g. fluorescent particles, are sufficiently small, then diffusion is fast enough for data acquisition from a great number of independent measurement volumes, and data acquisition using time averaging is nearly identical to ensemble averaging. However, if the characteristic time of diffusion is substantially longer than the time interval necessary for measuring fluorescence intensity (which is usually 10 to 50 μs), then active transport (flow or scanning) can considerably save time of data acquisition.

The measurement volumes can preferably be arranged on two-dimensional carriers, such as membranes or sheets having wells. Suitable carrier systems are e.g. described in WO 94/16313 (EVOTEC BioSystems GmbH). The measurement volumes might also be arranged in a linear way, as e.g. in a capillary system.

In fluorescence studies, it may be advantageous to take measures or reducing the background count rate, arising from Raman scattering in the solute material and dark count rate of the detector, with respect to the count rate per particle. In particular, it is in some cases preferred to use measurement volumes smaller than 100 $\mu m^3$, more preferably about 1 $m^3$. Advantageously, the high signal to background count rate and the small optical measurement volume may be achieved by using at least one microscope objective, preferably with a numerical aperture $\geqq 0.9$, in a confocal manner for both focussing an incident laser beam and collecting radiation, preferably light, emitted, scattered and/or reflected by units, preferably particles, in said samples. A confocal microscope set-up is preferably used which comprises at least one microscope objective, a dichroic mirror, a pin-hole in the image plane of said microscope objective, a detection means, a data acquisition means, and optionally means for scanning and/or actively transporting the sample. A suitable device is disclosed in WO 94/16313 (EVOTEC BioSystems GmbH). In a preferred embodiment the pin-hole might be replaced by an appropriate detector, as it is also described in WO 94/16313. It might further be preferred to choose a working distance between the microscope objective and the measurement volume in such a way that background contributions are minimized. Preferably, the working distance should be smaller than 1000 μm.

In a preferred embodiment of the method, multiple photon excitation is used to excite a particle. Multiple photon excitation means that the sum, difference or any combination of wave frequences of two, three or more photons is used for excitation of the secondary emission of the sample which can be e.g. luminescence or second order Raman scattering. Such an excitation scheme has an advantage in the sense that the excitation probability is not linearly dependent on excitation intensity, but on the second or higher power. Thus, the multiple photon excitation is mostly limited to the volume of the laser focus, whereas outside the laser focus no spurious excitation is generated. Appropriate laser sources of picosecond or subpicosecond pulses are well known to those of skill in the art. The present invention profits from such an excitation scheme in the sense that less background is generated compared to single photon excitation, and that there is no pinhole necessary to restrict the measurement volume. Thus, the pinhole diameter and its imaging on the detector do not enter as modelling parameters in the spatial brightness function any more.

In a further preferred embodiment, the measurement volume is restricted by the use of elements of near field microscopy. These can be used for focussing the excitation radiation of the units, and/or collecting the radiation emitted, scattered and/or reflected by the units. Near field optical microscopy means here that the light passes through an aperture with at least one of its dimensions being smaller than the wavelength of the light used and which is in direct contact to the measurement volume. The aperture may consist of an opaque layer with at least one hole of said diameter or at least one slit of appropriate width and/or a tapered glass fiber or wave guide with a tip diameter of said width, optionally coated with an opaque layer outside. A suitable device is disclosed in WO 96/13744 and in the German patent 44 38 391 (EVOTEC BioSystems GmbH).

Another preferred embodiment combines near field optical microscopy for the excitation light path, and conventional optical microscopy for the emission light path, or vice versa. The present invention profits from such a realization in the sense that the size of the measurement volume is reduced compared to conventional confocal microscopy.

Thus, the present invention can be used to measure higher particle concentrations as with other optical schemes.

A sample is usually characterized by values of concentration and specific brightness of one or more species of units, e.g. types of fluorescent particles. In cases when one or more of these values are known beforehand, the goal of analysis is to determine unknown values, either those of concentration, or specific brightness, or both.

Two alternative methods for selecting the model yielding a fit between the experimentally determined and calculated functions, preferably distributions of the number of photon counts can be used. In one embodiment, the well-known least squares fitting method, where the sample is described by a finite (usually small) number of parameters, can be employed. The purpose is to find values of the parameters yielding the closest fit between the experimental and the calculated curves. According to the invention, values of concentrations and/or specific brightnesses of a number of species of units, e.g. types of fluorescent particles, can be estimated. In a further embodiment, another general method called inverse transformation with linear regularization (ITR) can be employed. ITR describes the sample using a semi-continuous distribution function of units, preferably particles, versus their specific brightness, and searches for the closest fit demanding that the solution is a smooth function (For the method of ITR, see, e.g., W. H. Press, S. A. Teukolsky, W. T. Vetterling, B. P. Flannery, Numerical recipes in C: the art of scientific computing, second edition, Cambridge University Press, 1992, p. 808). It might further be preferred to use an inverse transformation with constraints (ITC) or an inverse transformation with regularization and constraints (ITRC). Because of statistical errors and limited sizes of measured data, inverse transformation is often an ill-posed mathematical problem, characterized by wild oscillations in its outcome. ITR, ITC and ITRC stabilize the mathematical problem by looking for a "regular" (e.g. a smooth) or constrained solution, for example by minimizing the sum of squared deviations of statistical data and a function of the solution itself, penalizing "irregular", usually irreproducible structures in the outcome, or values having no physical meaning. An example for constraining is disallowing negative values for concentration.

In the following, the invention is further illustrated in a non-limiting manner. Particularly, it is described how the expected distribution of the number of photon counts is determined.

A preferably many times repeated step in the calculation of the probability distribution of the number of photon counts is calculation of the probability distribution of the number of photon counts emitted, scattered and/or reflected by single species from a spatial section of the measurement volume with a constant value of spatial brightness. It is well known that the probability distribution of the number of particles in an open volume is Poissonian. Also, if the number of particles inside the spatial section is given, the number of detected photons per sampling time interval is Poisson distributed. Consequently, the overall distribution of the number of photon counts emitted, scattered and/or reflected by single species from a spatial section of constant brightness and detected by an ideal detector is compound Poissonian.

As the next step, one may study the case in which the measurement volume is divided into a number of spatial sections of constant brightness. If the values of volumes and spatial brightnesses in each of the sections are known, the distribution of the number of photon counts corresponding to each section can be determined separately. All these distributions are compound Poissonian. Furthermore, if distributions of the number of photon counts for all sections were known, the overall distribution can be determined through convolutions, using the fact that the total number of counts is the sum of the number of counts originating from different sections of the measurement volume.

As the following step, one may study a mixture of species, e.g. mixtures of fluorescent particles having different values of specific brightness. Each spatial section of the measurement volume can be divided into a number of abstract subsections each containing only particles of a single species. A similar procedure can be applied now as described above for spatial sections of the measurement volume in order to determine the overall distribution of the number of photon counts.

An experimentally determined distribution of the number of photon counts is ruled not only by properties of the light beam, but is influenced also by nonideal properties of the photon detector. Stochastically, the dark counts of the detector behave in the same manner as photon counts from background light of constant intensity. Their contribution are photon counts of Poisson distribution. Also, the way how the dead time of the detector and its afterpulsing distort the distribution of photon counts are known from literature on photon statistics (see e.g. B. Saleh, Photoelectron Statistics, Springer, Berlin, 1978).

In summary, the expected distribution of the number of photon counts is determined, from one side, by characteristics of the sample (concentrations and specific brightnesses of fluorescent particles of different kind), and, from the other side, by characteristics of the equipment (the sampling time interval, the spatial brightness function, the background count rate, the dead time and the afterpulsing probability of the detector).

In one embodiment, both the dead time and the afterpulsing probability of the detector are determined from experiments in which the distribution of the number of photon counts corresponding to light of constant intensity is determined. Correction for the dead time of the detector may be performed on the basis of a formula derived by Cantor and Teich (J. Opt. Soc. Am. 65, 786,1975; see also B. Saleh, p. 272–277). Mathematics of afterpulsing is simple: each photon pulse can be followed by another (artificial) pulse; this happens usually with a constant probability.

According to the invention, it is preferred that the spatial brightness function is characterized using experiments on a single species of particles. For example, if the laser wavelength 514.5 nm is used, then a solution of Rhodamine 6G is a convenient sample which can be used for characterizing the spatial brightness function.

What characteristics of the spatial brightness function can be employed when determining the expected distribution of the number of counts are values of volumes of the sections of the measurement volume corresponding to a selected set of values of the spatial brightness. Typically, a set of twenty or thirty values of the spatial brightness positioned at a constant distance from each other in the logarithmic scale have been selected, covering two or three orders of magnitude. Contribution from the lower brightness areas can be accounted for by a single parameter, their relative contribution to fluorescence intensity. Intensity fluctuations of this light can be neglected. Because of the large number of the sections of the measurement volume, it would be less preferred to consider volumes corresponding to each of the sections as independent variables. It is convenient to consider them as variables depending on a few other parameters, and determine the values of these parameters which yield the closest fit between the experimentally determined and the calculated distribution of the number of photon counts. Conveniently, a relatively simple model of the optical set-up is applied, which is not accounting for aberrations of the optics used, and which determines volumes of the sections of the measurement volume. For instance, the volumes of the sections depend on values of the convergence angle of the laser beam and the diameter of the pinhole. It might therefore be preferred to use the pinhole dimensions and the convergence angle of the incident laser beam as modelling parameters of the spatial brightness function.

Alternatively, simple mathematical expressions with formal parameters can be used instead of physical models for determining the volumes of spatial sections. The values of the formal parameters should preferably be selected in such a way that the closest fit between experimental and calculated distributions of the number of photon counts is achieved. Formal flexible expressions are advantageous because they yield a good fit between experimental and theoretical distributions of the number of photon counts. Secondly, calculations based on simple mathematical expressions are very fast compared to those based on physical models.

According to the invention, it may in some cases be preferred to select the length of the sampling time interval in such a way that in average more than one, preferably one to ten, counts per unit are yielded.

It may further be preferred that the length of the time interval is in average smaller than the characteristic correlation time of radiation intensity fluctuations.

If more than two unknown parameters of the sample have to be estimated, it is preferred to have no more than a few, preferably about one unit, preferably particle, per measurement volume.

It is preferred to have less than 10 units per measurement volumes to obtain good signal-to-noise ratios.

In one embodiment, at least one individual unit is statistically analyzed in terms of its specific brightness which may fluctuate or change non-stochastically.

The method of the present invention is particularly advantageous because information losses and distortions are kept minimal. Furthermore, a new quality attainable by the present invention is that the data processing depends less on a definite mathematical model of the sample compared to the other techniques which are state of the art. This means that the method is more reliable in terms of long term stability of an instrumental realization, and that any disturbation of the measurement volume by e.g. turbid samples or particles inside he laser beam does not significantly influence experimental results.

A further new quality attainable by the present invention is that the signal-to-noise ratio is much better compared to the techniques of the prior art. This means that experiments can be made within significantly shorter time (up to 100 fold shorter) than previously, showing the same signal-to-noise ratio as previous long term experiments. Since photobleaching of fluorescent molecules or fluorescently labelled molecules is an unsolved problem so far with any applied measurement technique in this field, especially when applied to cells, one is restricted to short measurement times. Thus, compared to the prior art, the present invention is advantageous for measurements inside cellular systems.

In one preferred embodiment, the present invention is realized in the field of fluorescence intensity fluctuation studies. The optical equipment is a conventional confocal FCS microscope equipped with a cw laser of visible light. The excitation laser beam is focused into a sample which is a homogeneous water solution of a low concentration, typically in the nanomolar range, of fluorescent material. Fluorescence emission from a microscopic confocal volume of about 1 $\mu m^3$ is collected on a photon detector. The measurement time which is typically 1 to 60 seconds is divided into hundreds of thousands time intervals of typical width of 10 to 50 $\mu s$. The highest number of photon counts typically obtained in this experimental realization of the invention herein described is between 10 and 100.

The method according to the present invention is particularly well suited for use in high throughput screening, diagnostics, monitoring of polymerization, aggregation and degradation processes, or analytics of nucleic acids.

In screening procedures, substances that are possibly pharmacologically active can be analyzed through their interaction with specific receptors by examining said interaction with binding of a luminescently labelled ligand to receptors wherein natural receptors on their carrier cells as well as receptors on receptor-overexpressing carrier cells or receptors on vesicles or receptors in the form of expressed molecules or molecular complexes may be used. Moreover, the interaction of substances with enzymes in solution or in their genuine cellular environment can be detected by monitoring a change of the substrate of the enzyme, e.g. a change in brightness. Further applications, especially concerning the performance of assays, are disclosed in WO 94/16313 (EVOTEC BioSystems GmbH).

For the detection of specific recognition reactions, potential active substances can be present in complex natural, synthetic or semisynthetic mixtures which are subjected to separation prior to analysis. These mixtures can be separated first e.g. by chromatography to test the individual fractions for the presence of functional compounds preferably "on line" in a capillary at the end of a separation matrix. The coupling of fractionating methods with FCS detection is described in detail in WO 94/16313 (EVOTEC BioSystems GmbH). A similar set-up can be used with respect to the present invention.

Often, aggregation and degradation are phenomena to be monitored. Aggregates display brightnesses different from the monomers and can be monitored according to the present invention.

In sequencing according to the method of Sanger, oligomers of different length, of which the terminating nucleic acid is labeled with a dye, are identified. Advanced techniques, as e.g. the one described in DE 38 07 975 A1, use dyes which exhibit different properties, such as fluorescence lifetime, according to the type of base they are attached to. The determination of a base is much more secure if several properties, such as fluorescence lifetime and brightness, or any other specific physical property, are determined and cross checked for consistency. In a preferred embodiment, the sample to be sequenced is separated by gel or capillary electrophoresis, or a separation step is conducted by capillary electro-chromatography, elecrohydrodynamic migration or related electrokinetic methods.

EXAMPLE 1

The nature and advantages of the invention may be better understood on the basis of the following example where a mixture of rhodamine dyes is analyzed. FIGS. 1 to 7 illustrate consecutive steps of the analysis and their results.

FIG. 1. Distributions of the number of photon counts experimentally determined at constant light intensities, time interval of 10 $\mu s$ and data collection time of 50 s. From curve fitting, the dead time of the detector was estimated to be 28±4 ns; afterpulsing probability 0.0032±0.0008. In the lower graph, weighted residuals of the curve fitting are presented.

FIG. 2. Distribution of the number of photon counts experimentally determined for a solution of rhodamine 6G at time interval of 40 µs and data collection time of 50 s.

FIG. 3. Normalized sizes of volumes of the twenty spatial sections of the measurement volume of the highest brightness. Section 0 corresponds to the maximal value of the spatial brightness while section 19 corresponds to about 100 times lower brightness. Sizes of volumes are determined from experiments on single fluorescent species.

FIG. 4. Residuals of curve fitting corresponding to an experiment on rhodamine 6G solution (the experiment graphed by FIG. 2).

FIG. 5. Distribution of the number of photon counts experimentally determined for three samples at time interval of 40 µs and data collection time of 50 s. The distribution corresponding to rhodamine 6G is the same as in FIG. 2.

FIG. 6. The results of the inverse transformation with linear regularization applied to the data of FIG. 5.

FIG. 7. Residuals corresponding to analysis of an experiment on the mixture solution of rhodamine 6G and tetramethylrhodamine (measured data in FIG. 5). Graph a: expected curve was obtained by inverse transformation with linear regularization. Graph b: expected curve was obtained by the least squares fitting of the experimental data. Graph c: residuals of the least squares curve fitting under a wrong assumption of single species.

As the first preparatory step of analysis, the dead time and the afterpulsing probability of the photon detector are estimated. This was done by determining the distribution of the number of photon counts under illumination of the detector by light of constant intensity. Since the dead time distortions are most noticeable at high count rates while the afterpulsing distortions are better resolved at low count rates, the values of the dead time and the probability of afterpulsing were determined by jointly fitting distributions of the number of photon counts determined at a relatively high and ad a relatively low illumination intensity. The experimentally determined count number distributions are presented in FIG. 1, together with residuals of the curve fitting. Values of the estimated parameters for the photon detector which have been used are: dead time 28 ns, afterpulsing probability 0.003.

The background count rate of the equipment is determined by measuring the count rate when the sample holder is filled with pure water.

As the second preparatory step, the spatial brightness distribution corresponding to a given optical set-up, was characterized. For that purpose, the distribution of the number of photon counts corresponding to a solution of rhodamine 6G was experimentally determined (FIG. 2). If the spatial brightness distribution is appropriately characterized, then the calculated curve fits the experimental curve. In order to numerically calculate the expected distribution of the number of photon counts, values of twenty one parameters characterizing the spatial profile are needed in our program: twenty sizes of volumes corresponding to twenty spatial sections of the highest values of spatial brightness, and the relative contribution to fluorescence light originating from areas of lower spatial brightness. In order to calculate values of these unknown parameters, a simple model of the optical equipment not accounting for aberrations was taken into use. As illustrated by FIG. 3, the determined sizes of the twenty volumes are reproducible, even if other species than rhodamine 6G are used.

Having determined values of the twenty one parameters characterizing the spatial brightness distribution in the way just described above, the calculated distribution of the number of photon counts indeed fits the experimentally curve, see FIG. 4.

After the preparatory steps described above the equipment is ready for analysis. In FIG. 5, distributions of the number of photon counts corresponding to three different samples are presented. In FIG. 6, the results of the inverse transformation with linear regularization are graphed. Both spectra corresponding to single species (rhodamine 6G or tetramethylrhodamine) have a single peak, but the peaks are centered at different values of specific brightness. The peak of rhodamine 6G is situated at about 108 kHz/molecule, whereas the peak of tetramethylrhodamine is centered at about 37 kHz/molecule. This indicates that a rhodamine 6G molecule is about 3 times brighter than a tetramethylrhodamine molecule. The spectrum corresponding to the mixture of the two species has two peaks centered indeed near the values obtained for the two species separately.

FIG. 7 illustrates the residuals corresponding to the measurements of the mixture of rhodamine 6G and tetramethylrhodamine. Different methods of data processing yield slightly different fit curves (and different residuals). The upper graph corresponds to the spectrum of specific brightness obtained by inverse transformation with linear regularization. The middle graph corresponds to the fit curve obtained assuming two species. These two graphs are nearly identical. The experimentally determined distribution of the number of photon counts can formally be fitted under the wrong assumption of single species, which is shown in the lower graph, but the fit curve is obviously apart from the experimental one.

EXAMPLE 2

To further demonstrate the usefulness of the present invention, a hybridization process was studied using a conventional confocal FCS microscope. A model system based on the interaction of two 32-base oligonucleotides, both labelled with the fluorescent dye TAMRA (5- (and 6-) carboxytetramethylrhodamine), has been investigated. The sequence of these oligonucleotides included a site for the restriction enzyme EcoRI enabling the cleavage of the primer dimer. This restriction analysis was used as a control in order check the specificity of the results obtained by the method according to the present invention.

The hybridization was performed in a 10 mM Tris buffer (pH 7.4) containing 1 mM EDTA and 100 mM NaCl, the restriction analysis in 50 mM Tris-HCl (pH 7.5), 10 mM $MgCl_2$, 100 mM NaCl, 0.2% Triton X-100. The measurement time for each analysis was 30 seconds.

FIG. 8. Number of particles per volume element as a function of their specific brightnesses.

The analysis of the TAMRA-labelled single-strand oligonucleotides revealed a single characteristic fluorescence intensity peak of 45 kHz for oligonucleotide A (FIG. 8a), and of 20 kHz for oligonucleotide B (FIG. 8b) upon excitation at 543 nm.

The hybridization of the oligonucleotides A and B resulted in a single intensity peak of 35 kHz (FIG. 8c) indicating that the hybridization was complete. From the intensity values of the individual oligonucleotides, one would have expected an intensity peak of 65 kHz for this primer dimer. This discrepancy in the intensity can be explained by the occurrence of dye-nucleotide interactions and electron transfer-induced quenching.

Further evidence that the 35 kHz intensity peak represents the primer dimer is given by an cleavage experiment using EcoRI (FIG. 8d). Restriction cleavage of the annealed primers results in an intensity peak of 20 kHz. The broadening of the intensity distribution indicates that the reaction was not complete.

These experiments demonstrate that the method according to the present invention is well-suited for studying hybridization processes which play an important role for the detection and characterization of pathogens. The ability of the method according to the present invention to measure the activity of a restriction endonuclease was also demonstrated by this series of experiments.

EXAMPLE 3

Biotin labelled with the following different dyes
a) 5- (and 6-) carboxy-X-rhodamine (abbr. ROX)
b) 5- (and 6-) carboxytetramethylrhodamine (abbr. TAMRA)
c) Rhodol Green™
d) Rhodamin Green™
e) Resorufine
f) Texas Red and
g) Rhodamine B with and without a spacer molecule (abbr. Sp.) as well as their mixtures with streptavidin have been analyzed according to the method of the present invention in order to monitor quenching effects of differently labelled biotin upon streptavidin binding.

FIG. 9 shows the specific brightnesses of the different molecules. The presence of streptavidin is indicated by "+", whereas its absence is indicated by "−".

EXAMPLE 4

The following example proves that the method according to the present invention is valid for the measurement of ligands bound to receptor populations on membrane vesicles.

The use of crude biological material such as biomembranes derived from tissue or cells in assays to be analyzed by single particle fluorescence detection analysis brings along issues dealing with the nature and heterogeneity of this material. When membrane preparations are generated from receptor-overexpressing cells, the most probable situation will be that there are many receptor molecules on a single membrane vesicle. For an analysis of fluorescent ligand binding to those receptors, the method according to the present invention is ideally suited because it discriminates between particles which display different fluorescence intensities. Membrane vesicles are slowly moving particles (mean diffusion time $T_{diff} > 10$ ms) in a low concentration. Thus to attain a reasonable signal-to-noise ratio, the measurement times for these rare events have to be prolonged compared to nanomolar fluorophore solutions. In order to shorten measurement time and improve statistical accuracy, the effective volume to be analyzed had to be increased substantially without loosing the advantage of detecting single molecules. This has been achieved by introducing a beam scanning device. Using a beam scanner also circumvents bleaching effects since the mean excitation time of a single vesicle is minimized by the movement of the laser beam.

The feasibility to quantify a biological interaction by the method according to the present invention as demonstrated using epidermal growth factor (abbr. EGF) binding to membrane vesicles from A431 human carcinoma cells. These cells express $10^5$ to $10^6$ epidermal growth factor receptors per cell.

Membrane Vesicle Preparations

Membrane preparations were carried out by cell disruption in a hypotonic buffer (20 mM Tris/HCl, pH 7.5, 5 mM $MgCl_2$) containing protease inhibitors (leupeptin, aprotinin and PMSF) using a glass homogenizer and high-spin centrifugation after removal of nuclei at low g force. 10% sucrose was added during the first centrifugation step. The membranes were homogenized in EGF binding buffer (20 mM HEPES pH 7.4, 140 mM NaCl, 5 mM $MgCl_2$, 1.8 mM CaCl, 4.2 mM $NaHCO_3$ and 5.5 mM glucose) using a Branson sonifyer prior to the experiment. Protein content was determined with bicinchoninic acid (PIERCE) to 0.504 mg/ml (A431).

EGF Binding Studies

Binding experiments using EGF labelled with tetramethylrhodamine (abbr. TMR) and A431 membranes were performed according to Carraway et al. (J. Biol. Chem. 264: 8699,1989). Briefly, they were diluted with EGF binding buffer and were incubated with labelled ligand in 20 μl samples for 40 minutes at room temperature. In competition experiments, membranes were incubated with unlabelled EGF. Measurements of 30 seconds duration were carried out using one-dimensional beam scanning at 25 Hz and an amplitude of 700 μm.

FIG. 11 shows examples of intensity distributions measured at certain concentrations of A431 vesicles.

The y-axis of the intensity distributions in FIG. 11 is constructed by multiplying the particle number obtained for each intensity in the grid of intensities by the intensity of that grid point, thus representing the contribution of particles at that intensity to the total intensity. It is preferred to choose this transformation as it emphasizes on particles with high intensity, but low concentration which is the case for vesicles with bound ligand. In terms of particle numbers (concentration), vesicles would only make a negligible contribution.

FIG. 11a shows the intensity distribution of the ligand alone. The ligand has an intensity of about 40 kHz/particle. In FIGS. 11b–d, intensity distributions with increasing concentrations of vesicles are plotted. The increase of fluorescence from bright particles, i.e. vesicles with many ligand-receptor complexes on them, is clearly visible.

In order to quantify the degree of binding, one has to distinguish between unbound ligand and ligand-receptor complexes. Vesicles with several bound ligands are brighter than the ligand alone. Thus, a certain discriminating intensity $I_d$ is chosen. Particles detected below this intensity are assumed to be ligand molecules, while particles detected above this intensity are counted as vesicles with receptor-ligand complexes.

The concentration $c_L$ of free ligand is determined by summing up over all concentrations below the discriminating intensity:

$$c_L = \sum_{\forall i: I_i < I_d} c_i$$

The concentration $C_{RL}$ ligand-receptor complexes is given by the assumption that a vesicle with n bound ligands has an intensity of n times the ligand intensity. Thus, an intensity component at an intensity I is from a vesicle with $n=I/I_{Ligand}$ ligand-receptor complexes, and the concentration of these complexes is given by $$c_{RL} = \sum_{\forall i: I_i \geq I_d} c_i \frac{I_i}{I_{Ligand}}$$

Now, the degree of complex formation is given by $$complex = \frac{c_{RL}}{c_L + c_{RL}}$$

Figure 1:
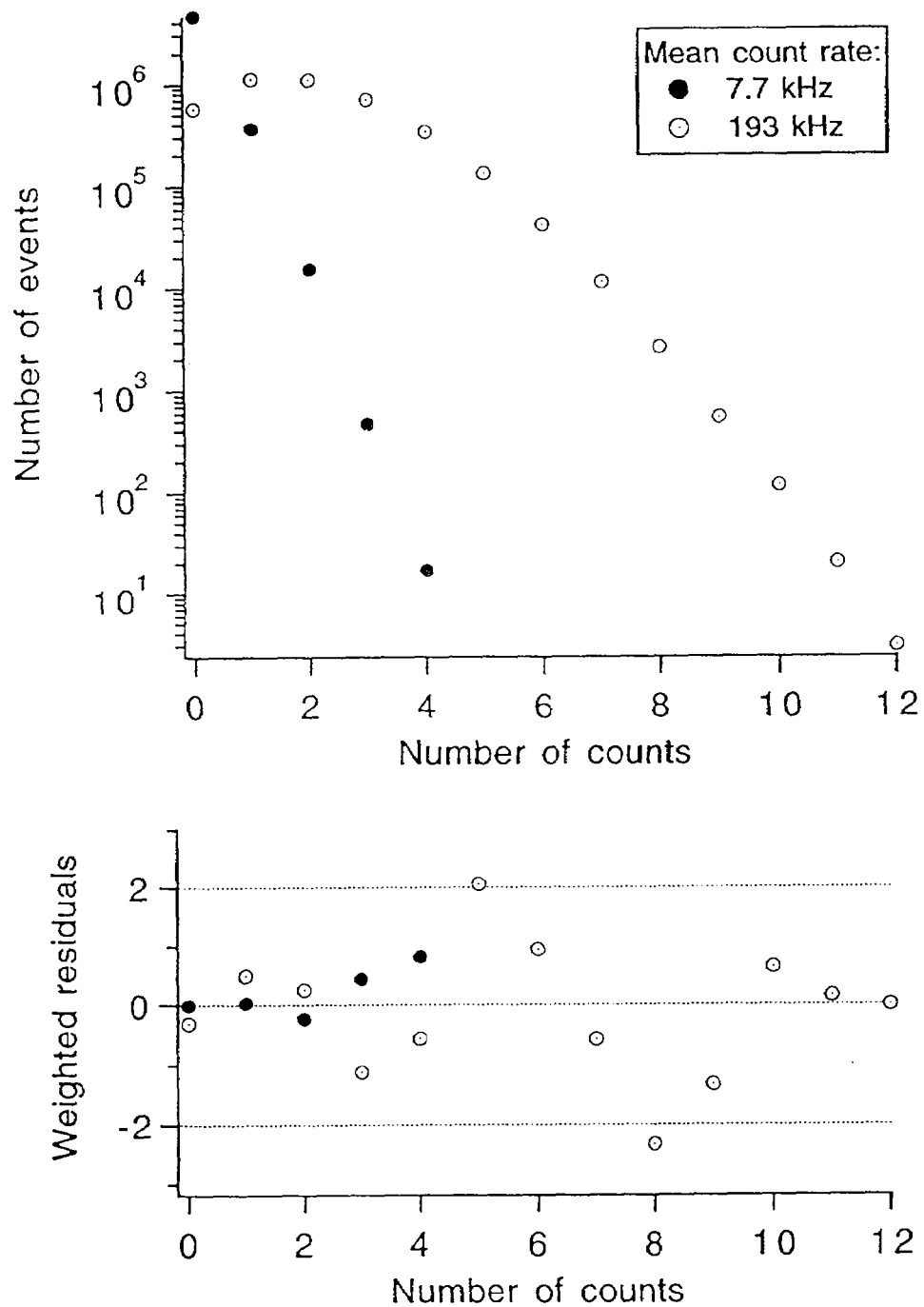
Figure 2:
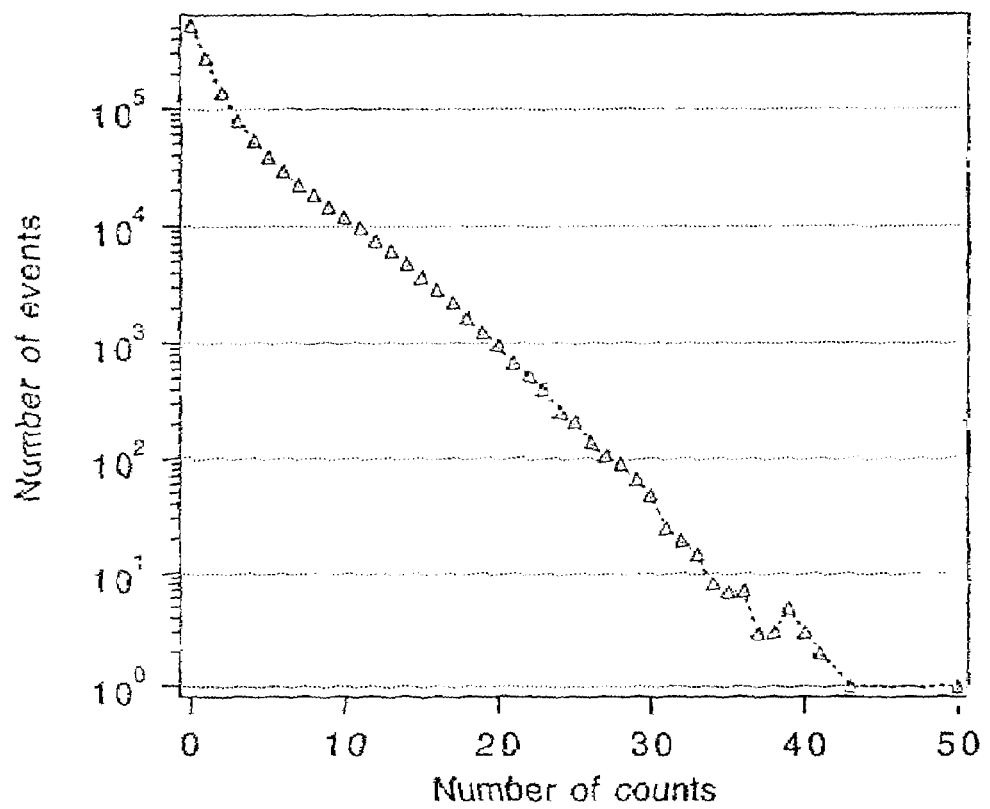
Figure 3:
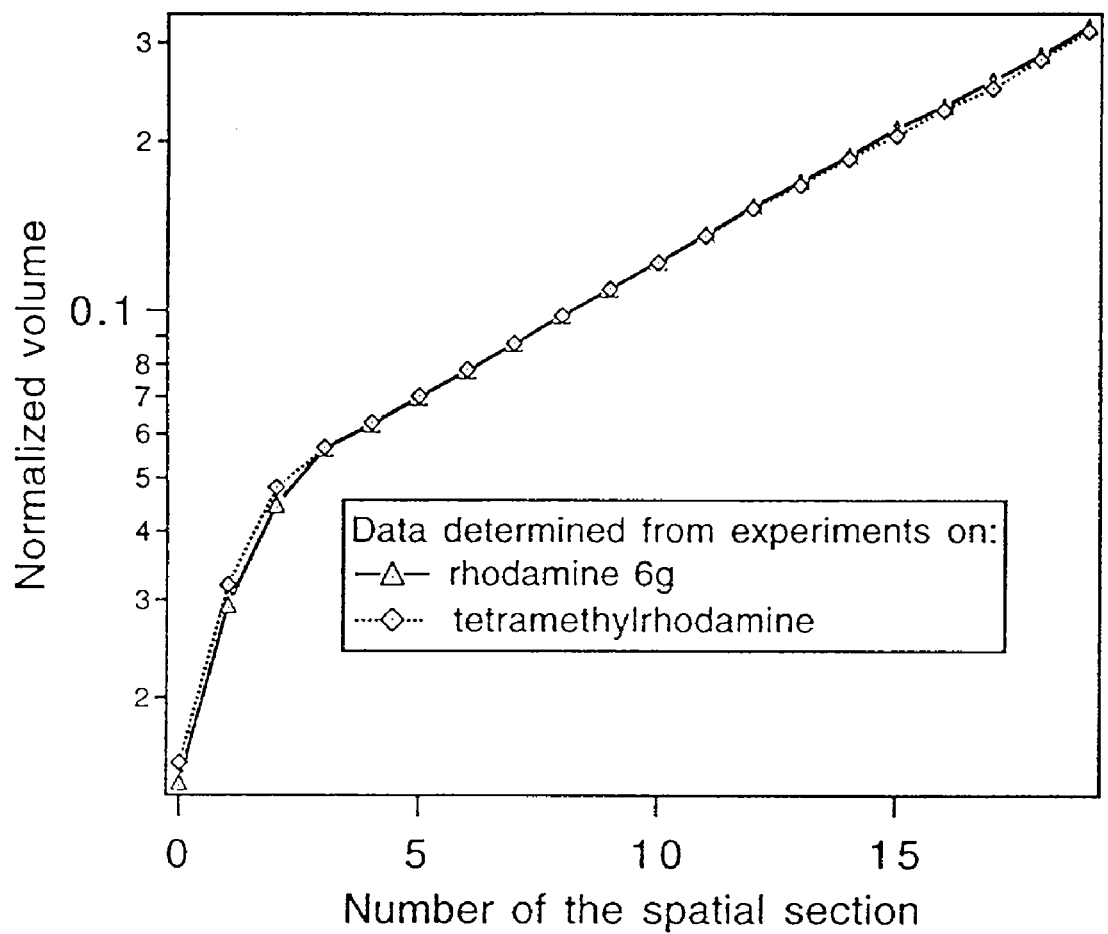
Figure 4:
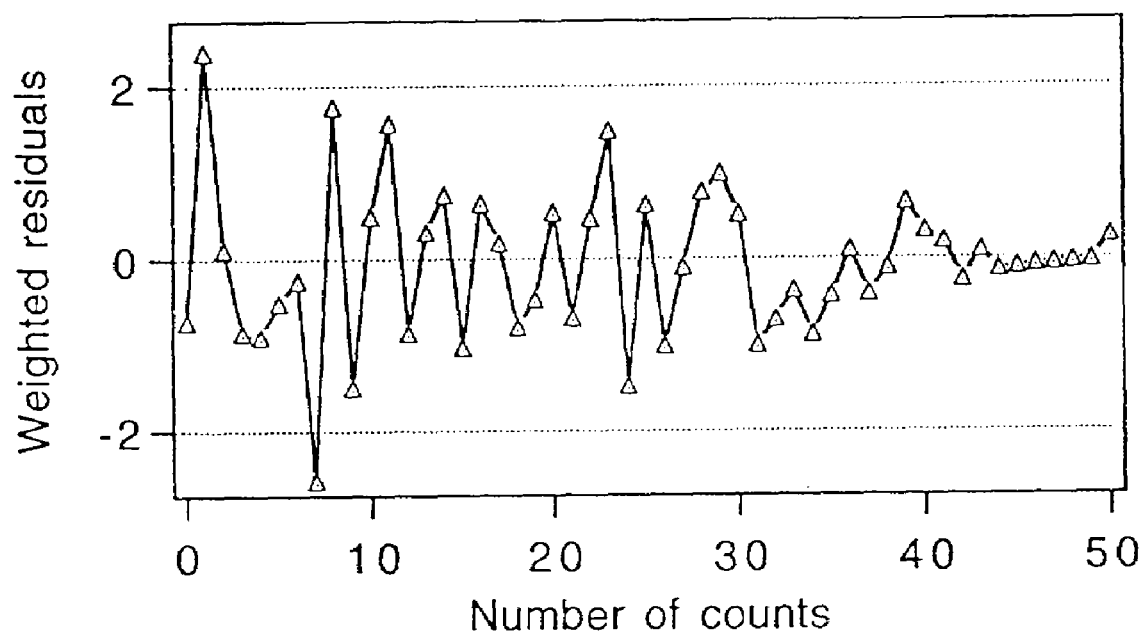
Figure 5:
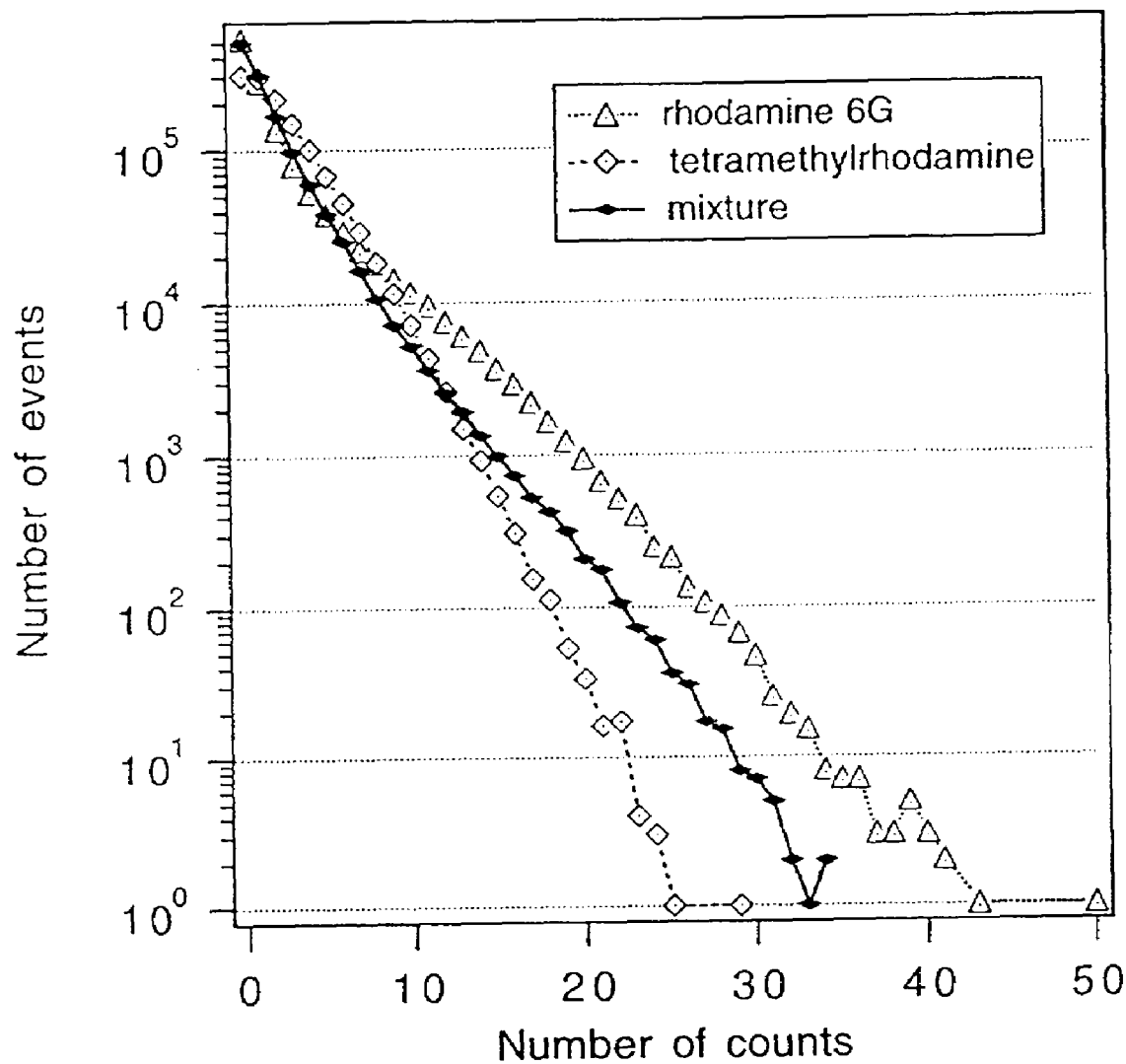
Figure 6:
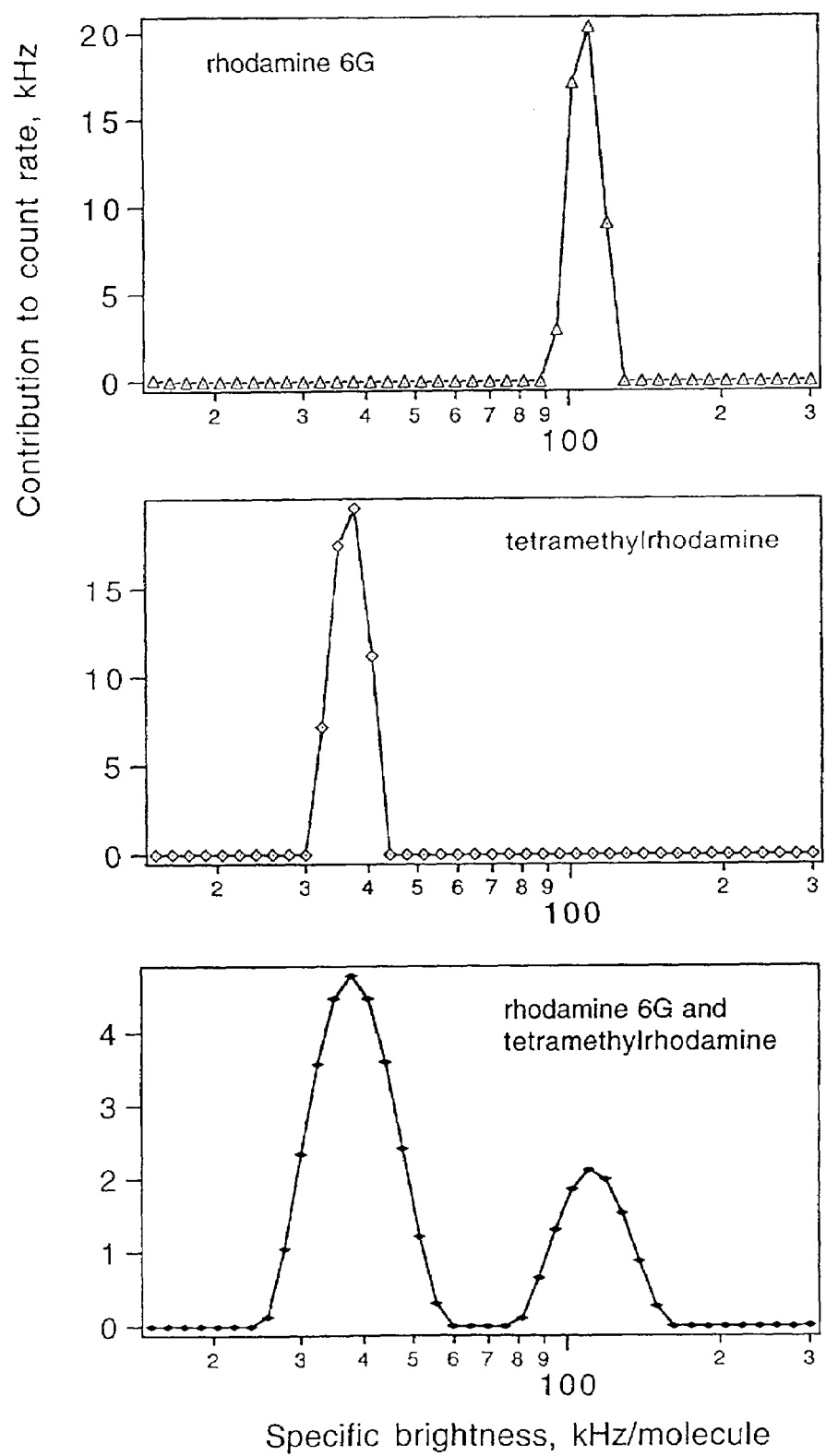
Figure 7:
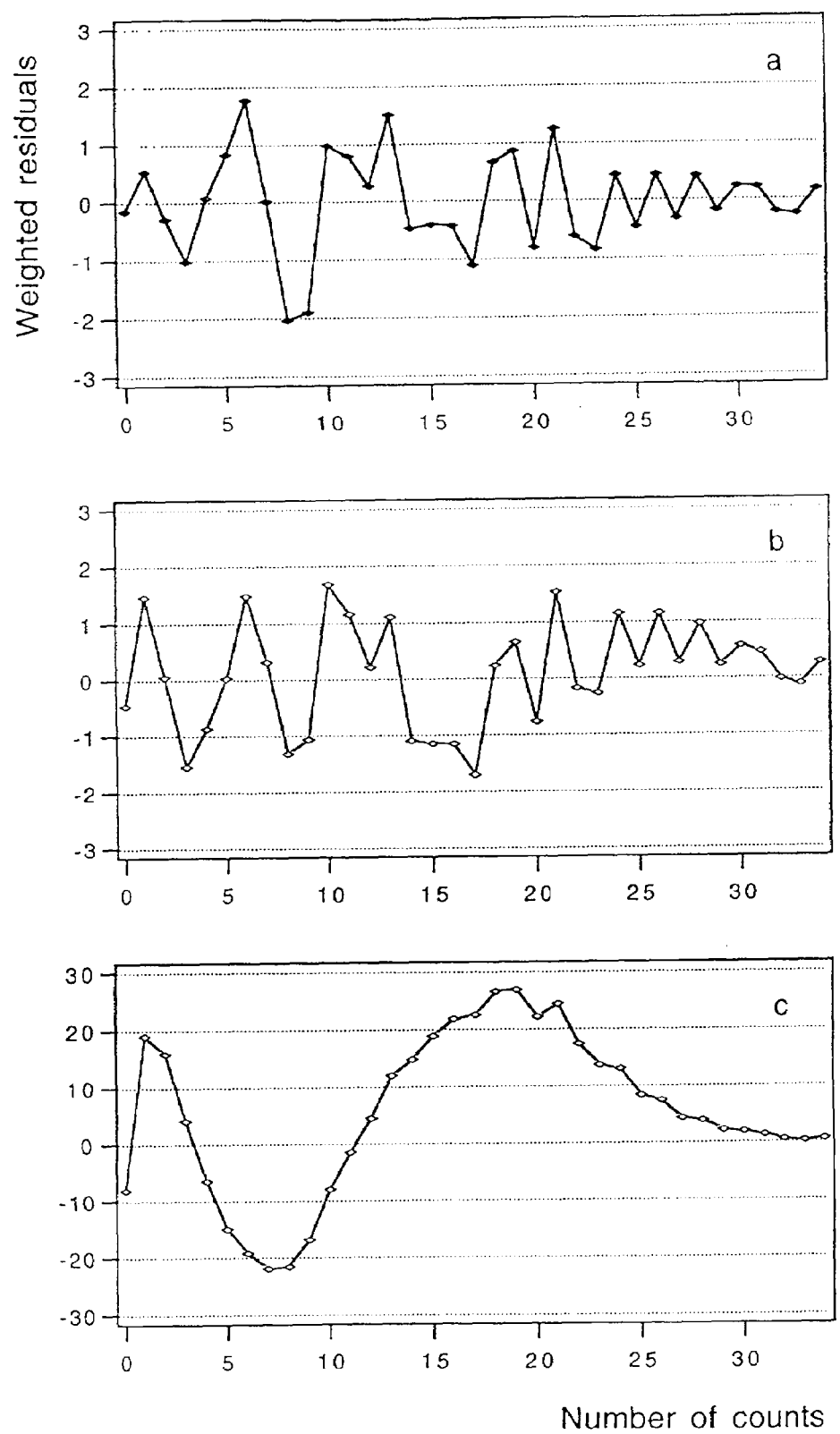
Figure 8A:
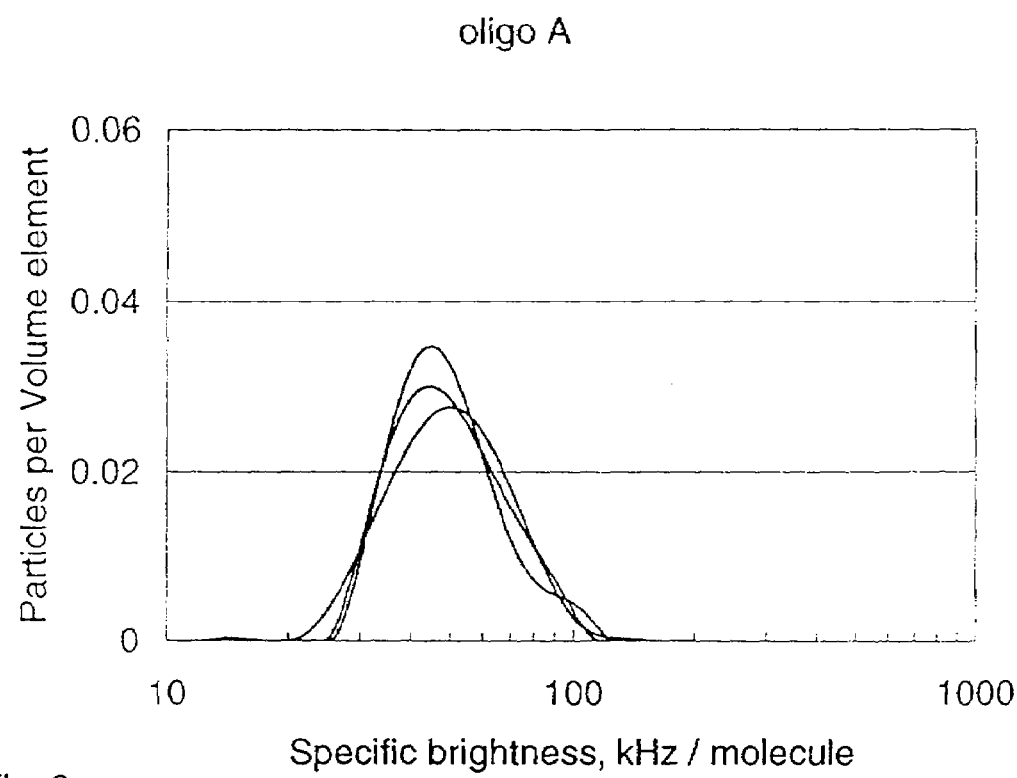
Figure 8B:
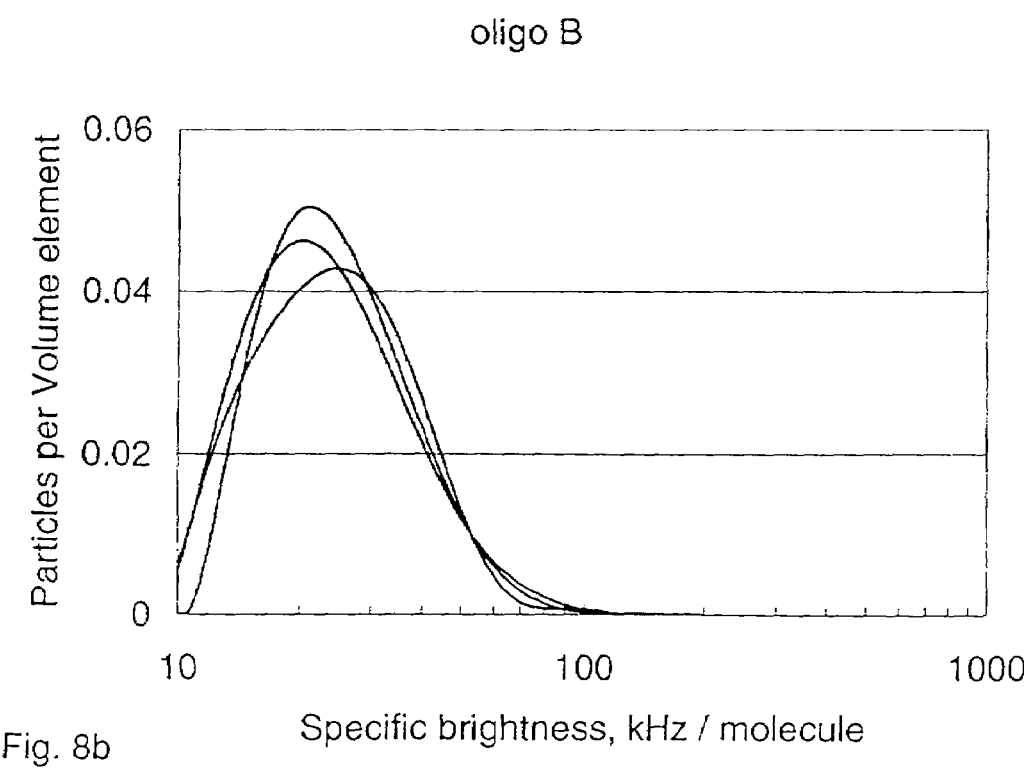
Figure 8C:
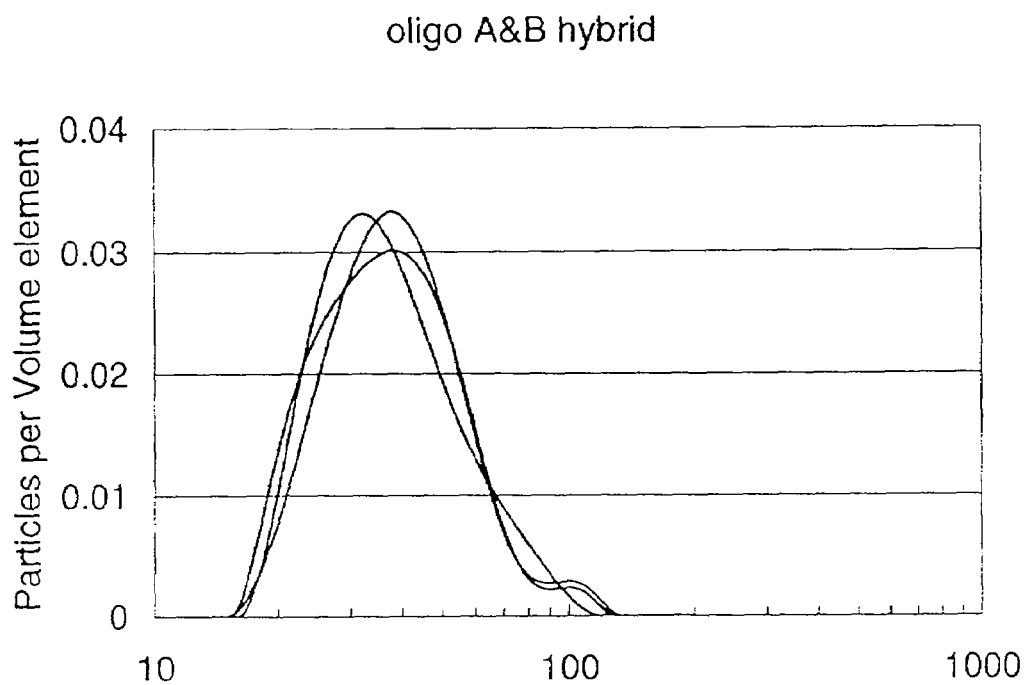
Figure 8D:
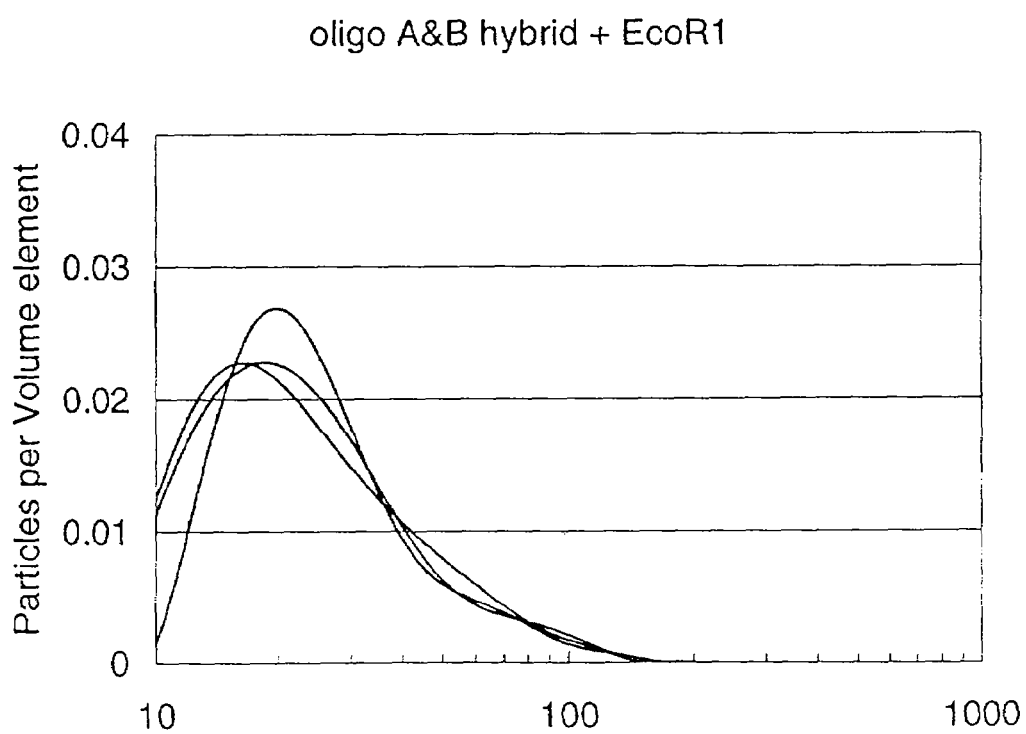
Figure 9:
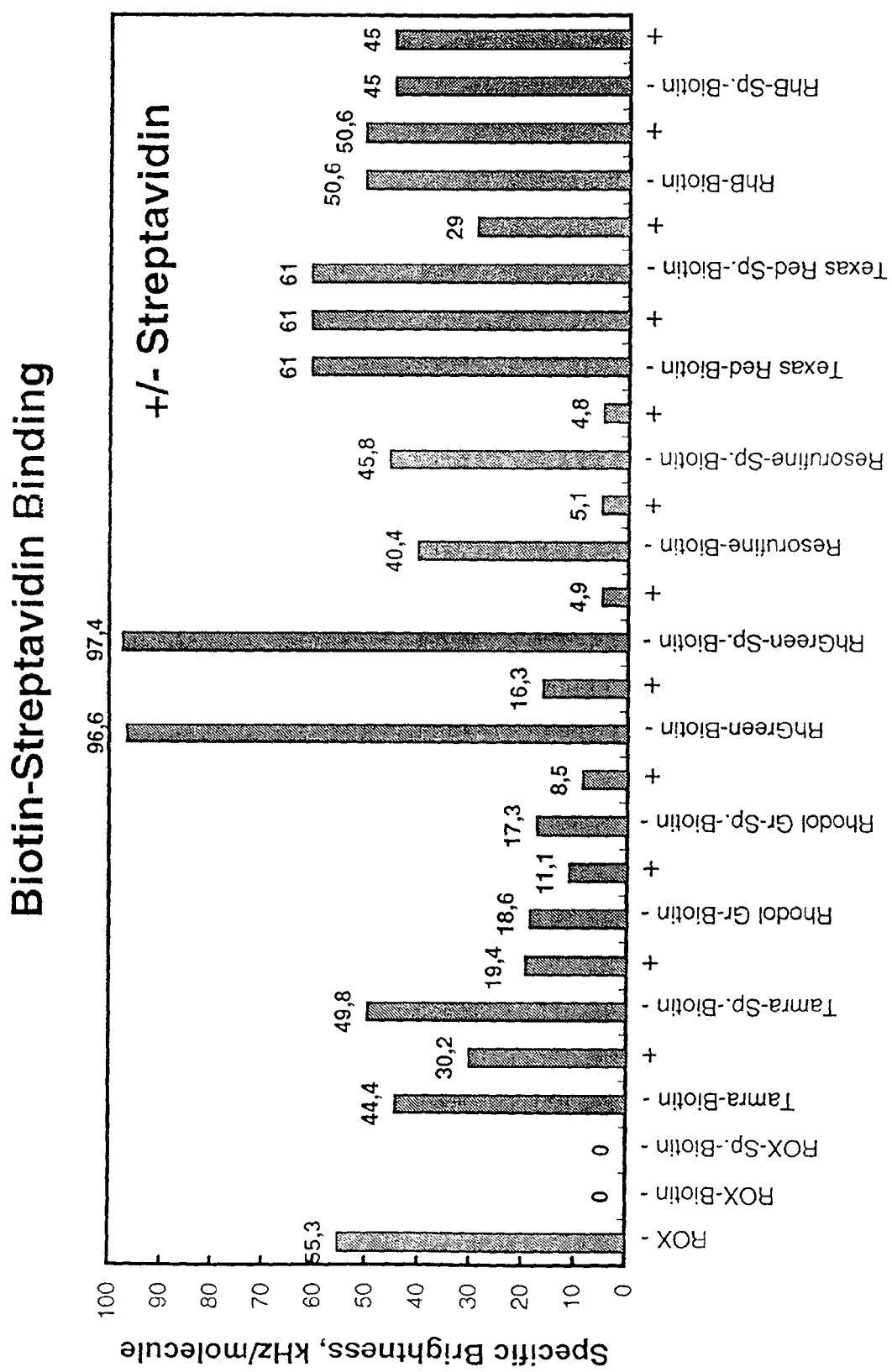
Figure 10:
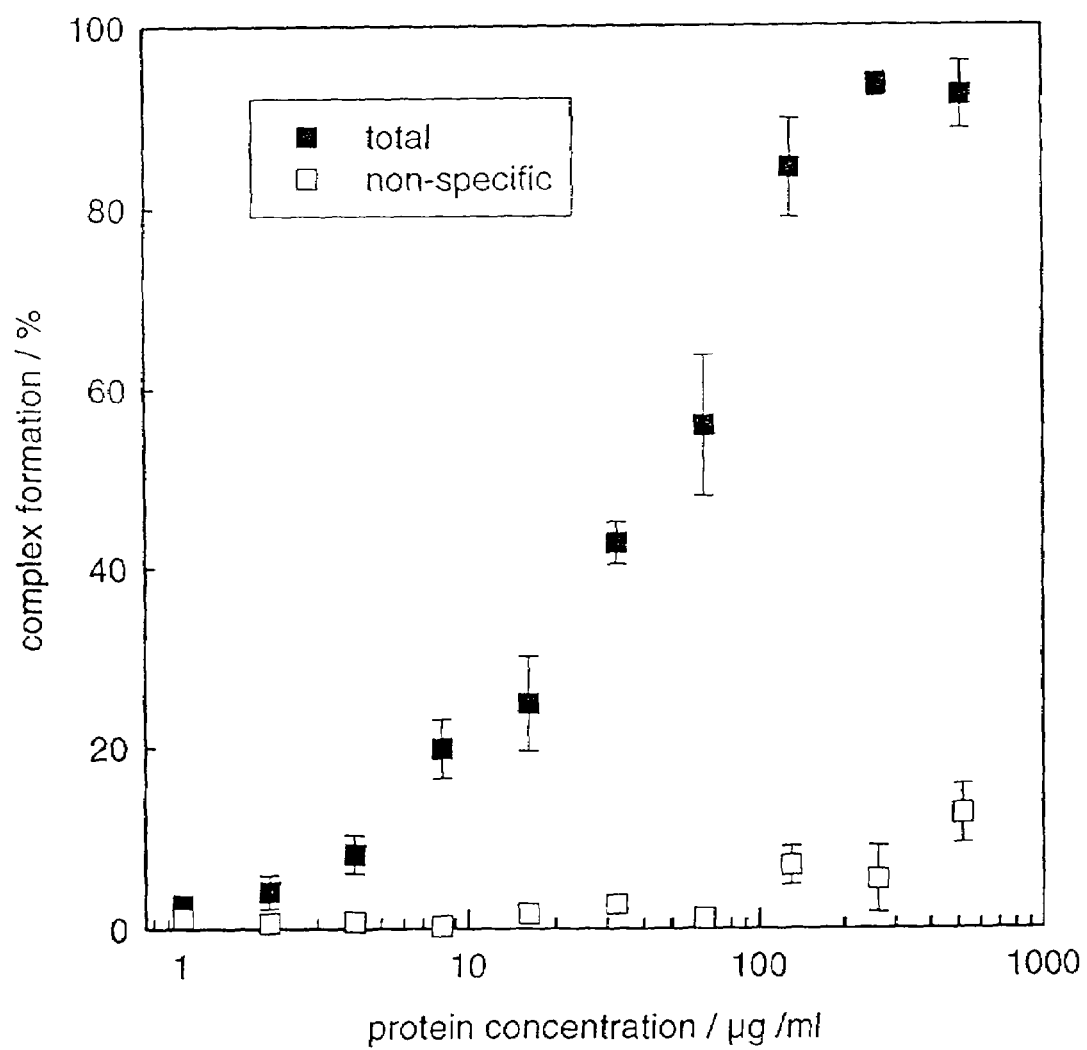
FIG. 10 shows a plot of the amount of ligand-receptor complexes in relation to the total ligand concentration.

This is plotted in FIG. 10 for the binding of labelled EGF to A431 vesicles.

The invention claimed is:

1. A method for analyzing a sample involving detecting radiation from particles or molecules in a measurement volume of the sample, the method comprising the steps of:
measuring by detection means, in a repetitive mode, a number of photon counts per time interval of defined length,
determining an experimental distribution function of the number of photon counts measured per time interval,
determining a distribution function of specific brightness of the particles or molecules based on the experimental distribution function of the number of photon counts measured, by fitting an expected distribution function of the number of photon counts against the experimental distribution function of photon counts, wherein the expected distribution function of the number of photon counts is calculated using characteristics of a spatial brightness function, employing values of volumes of sections of the measurement volume corresponding to a selected set of values of the spatial brightness function and considering the volumes as variables depending on modeling parameters of the spatial brightness function, and selecting the values of these modeling parameters which yield the closest fit between the experimentally determined and the expected distribution of the number of photon counts.

2. The method according to claim 1, wherein radiation from particles or molecules in one or more measurement volume(s) is measured.

3. The method according to claim 1, wherein the detection means is part of a confocal microscopic set-up further having:
at least one microscope objective having an image plane for both focusing an incident laser beam and collecting radiation emitted, scattered and/or reflected by the particles or molecules of the sample,
a dichroic mirror,
a pinhole in the image plane of the microscope objective, and data acquisition means.

4. The method according to claim 3, wherein dimensions of the pinhole are used as a modeling parameter of the spatial brightness function.

5. The method according to claim 3, wherein the incident laser beam has a convergence angle used as a modeling parameter of the spatial brightness function.

6. The method according to claim 3, wherein the confocal microscopic set-up further comprises means for scanning and/or moving the sample.

7. The method according to claim 3, wherein the at least one microscope objective has a numerical aperture=0.9.

8. The method according to claim 1, wherein the particles are molecular aggregates, complexes, vesicles, cells, viruses, bacteria, beads, or mixtures thereof in solids, liquids or gases.

9. The method according to claim 1, wherein the particles or molecules can be grouped into species distinguished by their specific brightness.

10. The method according to claim 9, wherein at least one of the species is luminescent.

11. The method according to claim 9, wherein at least one of the species is luminescently labeled.

12. The method according to claim 9, wherein at least one of the species is fluorescent.

13. The method according to claim 1, wherein the particles carry binding sites for luminescent molecules.

14. The method according to claim 2, wherein the sample has a volume, and the measurement volume is less than the volume of the sample.

15. The method according to claim 14, wherein the measurement volume is $\leq 10^{-12}$ l.

16. The method according to claim 14, wherein the particles or molecules move into and out of the measurement volume during measuring.

17. The method according to claim 14, wherein the particles or molecules are optically scanned.

18. The method according to claim 2, wherein the measurement volumes are arranged two-dimensionally.

19. The method according to claim 18, wherein the measurement volumes are arranged on a membrane or a sheet having wells.

20. The method according to claim 2, wherein the measurement volume is restricted by the use of elements of near field optical microscopy, or elements of near field optical microscopy in combination with conventional microscopy optics.

* * * * *

UNITED STATES PATENT AND TRADEMARK OFFICE
CERTIFICATE OF CORRECTION

| | | |
|---|---|---|
| PATENT NO. | : 7,019,310 B2 | Page 1 of 1 |
| APPLICATION NO. | : 09/029830 | |
| DATED | : March 28, 2006 | |
| INVENTOR(S) | : Peet Kask | |

It is certified that error appears in the above-identified patent and that said Letters Patent is hereby corrected as shown below:

Title page, item 22, PCT filed: Change "Nov. 10, 1997" to October 11, 1997

Signed and Sealed this

Eleventh Day of July, 2006

JON W. DUDAS
*Director of the United States Patent and Trademark Office*